(12) United States Patent
Konstorum et al.

(10) Patent No.: US 8,795,290 B2
(45) Date of Patent: Aug. 5, 2014

(54) EAR PRESSURE EQUALIZING TUBE AND INSERTION DEVICE

(71) Applicant: Gyrus ACMI, Inc., Southborough, MA (US)

(72) Inventors: Gregory S. Konstorum, Stamford, CT (US); John S. Duran, Brewer, ME (US); Antonio E. Prats, Shrewsbury, MA (US); Lawrence J. St. George, Sudbury, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 13/773,778

(22) Filed: Feb. 22, 2013

(65) Prior Publication Data

US 2014/0100584 A1    Apr. 10, 2014

Related U.S. Application Data

(60) Provisional application No. 61/710,195, filed on Oct. 5, 2012.

(51) Int. Cl.
*A61F 11/00*    (2006.01)

(52) U.S. Cl.
USPC ........................................ 606/109; 604/264

(58) Field of Classification Search
USPC ........ 606/108, 109, 170, 171; 604/19, 27, 35, 604/93.01, 118, 119, 264, 128, 129, 156, 604/157, 158, 163, 164, 173; 623/10; 123/108, 109, 170, 171
See application file for complete search history.

(56) References Cited

U.S. PATENT DOCUMENTS

| | | | |
|---|---|---|---|
| 3,530,860 A | 9/1970 | Majoros | |
| 3,948,271 A | 4/1976 | Akiyama | |
| 4,650,488 A | 3/1987 | Bays et al. | |
| 5,053,040 A | 10/1991 | Goldsmith, III | |
| 5,254,120 A | 10/1993 | Cinberg et al. | |
| 6,527,780 B1 | 3/2003 | Wallace et al. | |
| 7,704,259 B2 | 4/2010 | Kaplan et al. | |
| 7,766,163 B2 * | 8/2010 | Tanghoej | 206/364 |
| 8,052,693 B2 | 11/2011 | Shahoian | |
| 8,398,664 B2 * | 3/2013 | Lamps et al. | 606/181 |
| 8,574,240 B2 * | 11/2013 | Loushin et al. | 606/109 |
| 2009/0209972 A1 | 8/2009 | Loushin et al. | |
| 2009/0299379 A1 | 12/2009 | Katz | |

FOREIGN PATENT DOCUMENTS

| | | | |
|---|---|---|---|
| WO | 2005/115527 A2 | 12/2005 | |
| WO | 2006/119512 A2 | 11/2006 | |
| WO | 2011/008948 A1 | 1/2011 | |

OTHER PUBLICATIONS

PCT Search Report & Written Opinion dated Oct. 14, 2013; Appl. No. PCT/US2013/055516.

* cited by examiner

*Primary Examiner* — Dianne Dornbusch
*Assistant Examiner* — Robert Lynch
(74) *Attorney, Agent, or Firm* — The Dobrusin Law Firm, PC

(57) ABSTRACT

Improved ear ventilation tubes and spring loaded insertion devices for use with the ventilation tubes whereby perforation and insertion steps take place substantially simultaneously with an aspiration step following.

18 Claims, 7 Drawing Sheets

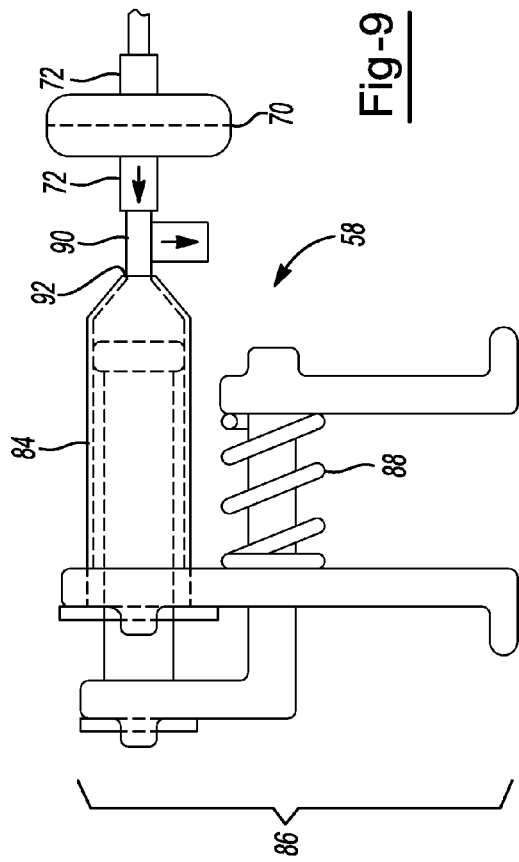
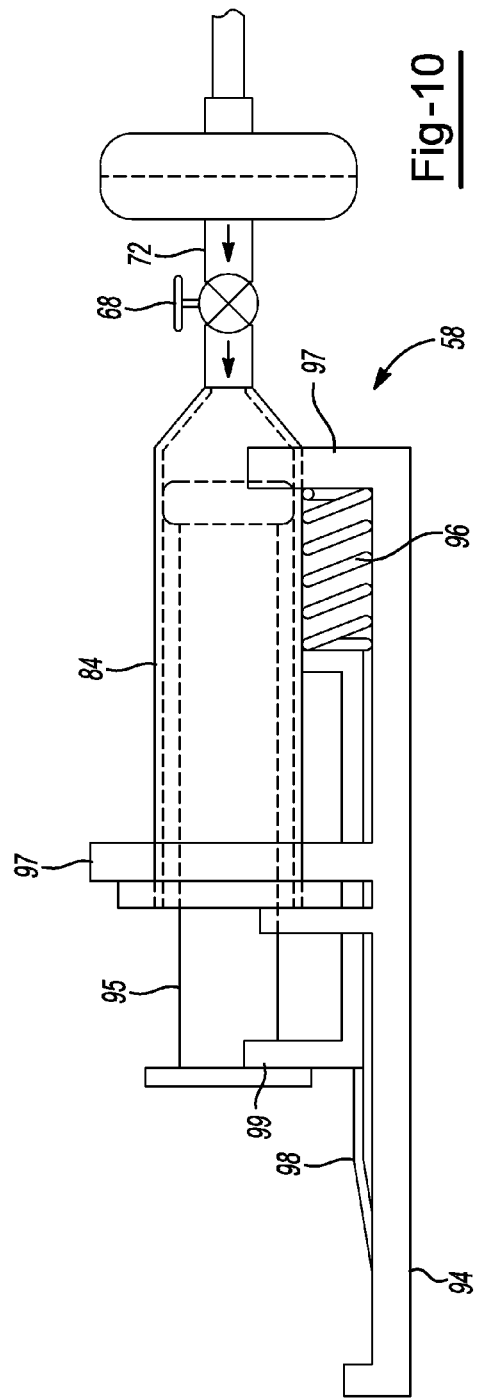

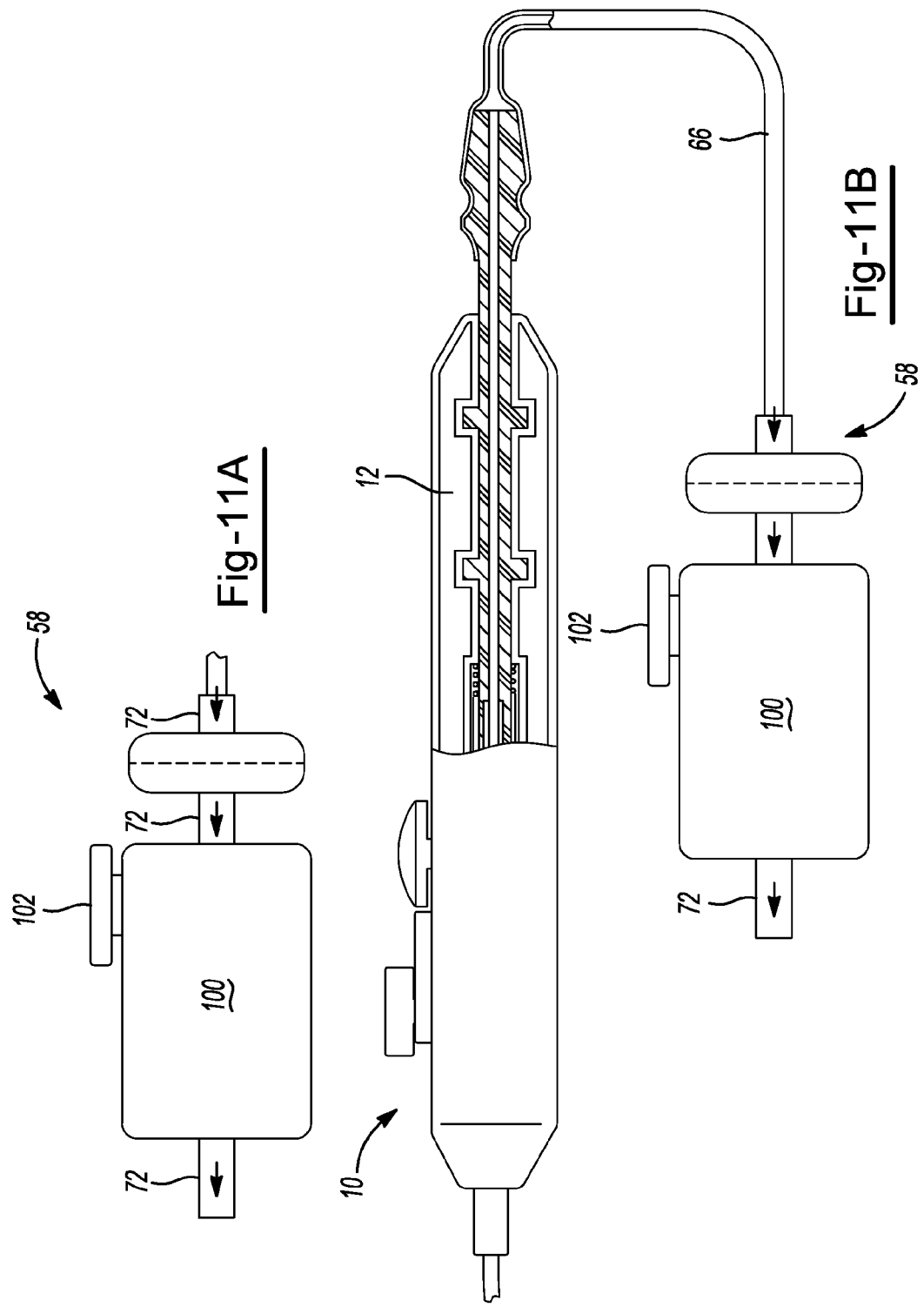

EAR PRESSURE EQUALIZING TUBE AND INSERTION DEVICE

FIELD OF THE INVENTION

The present invention relates generally to an improved ear ventilation tube insertion device and ventilation tubes associated therewith.

BACKGROUND OF THE INVENTION

There are a number of approaches to treating ear passage inflammation. One of the more common treatments is the insertion of ear ventilation tubes in an effort to permit the passage of fluid within the ear canal. While beneficial, the tube insertion process can cause substantial discomfort especially to young patients who are the most common recipients of the tubes.

One approach is to utilize devices that both perforate the tympanic membrane and insert the ventilation tube in a nearly simultaneous step. One example is described in U.S. Pat. No. 3,530,860 where an elongated instrument includes a tip for manually perforating the tympanic membrane, the device further fitted with a drain tube just below the tip. A second member is utilized to locate the drain tube into the opening created by the tip. U.S. Pat. No. 5,053,040 teaches ventilation tubes having a conical end corresponding to a conical end of a separate tip for piercing the eardrum, where the tip is manually retracted upon insertion of the ventilation tube. U.S. Pat. No. 8,052,693 discloses a combined tympanic membrane penetrator and ventilation tube delivery device. A lance at its distal end penetrates the tympanic membrane and the lance can thereafter be retracted to deploy a ventilation tube. U.S. Pat. No. 5,254,120 discloses a spring-loaded protector movably mounted on a ventilation tube for retracting in a proximal direction to expose a blade during an incising of a tympanic membrane.

Despite the approaches discussed above, there is still a need for devices that provide for near simultaneous perforation, ventilation tube insertion and aspiration. Many existing devices continue to require discrete perforation and insertion steps, which prolongs the insertion and the associated discomfort. Further, many existing approaches require manual perforation leaving room for error. There continues to be a need for insertion devices and ventilation tubes that minimize the time between perforation and ventilation tube insertion, provide aspiration, and perform more automated perforation and insertion steps.

SUMMARY OF THE INVENTION

The present invention meets one or more of the above needs by providing a device fitted with specialized ventilation tubes that are formed to include a perforating blade or receive a perforating blade. The device may comprise a rigid shaft having a first terminal end, a second terminal end and a flexible to substantially enclosed within the rigid shaft. The device may further include a spring-loaded plunger, at least a portion of which is located within the flexible tube. In addition, the device may include a plunger release button adapted for engaging the plunger and releasing the plunger that upon depression of the release button, the plunger extends beyond the first terminal end of the rigid shaft. A plunger retrieval button may also be located adjacent the plunger release button for returning the device to a ready position. A control opening may be located within the plunger retrieval button and a plunger retrieval button suction hole may be located along a top portion of the plunger retrieval button so that the control opening is substantially aligned with the plunger retrieval button suction hole during depression of the plunger release button. A suction connector may further be included and located adjacent the second terminal end of the rigid shaft and adapted for receiving a suction tube.

The device may be adapted to receive ventilation tubes that are fitted with a perforating blade that is permanently connected to the tube. The device may be adapted to receive ventilation tubes that facilitate movement of a perforating blade therethrough.

The teachings of the present invention envision a method of using the devices described herein including the steps of providing a device in a ready position; locating a ventilation tube within a transparent shaft tip, the transparent shaft tip being attached to a first terminal end of a rigid shaft and the rigid shaft containing at least a portion of a plunger assembly; placing at least a portion of the ventilation tube proximate an ear canal; depressing a plunger release button with special features (flats) engaged with corresponding plunger features, whereby the movement of the plunger release button causes a release of the plunger flats. Depression of the plunger release button allows a compressed plunger spring to push the plunger assembly forward so that the ventilation tube enters into the ear canal; and sliding a plunger retrieval button toward the proximal end of the device to return the device to the ready position.

As will be seen, the devices and methods taught herein offer automated perforation and insertion in a nearly simultaneous process by activation of a single button as well as aspiration.

DESCRIPTION OF THE DRAWINGS

FIG. 8b is a perspective view of a modified version of the portable vacuum device of FIG. 8a.

FIG. 9 is a cross-sectional side profile view of an illustrative portable vacuum device in accordance with the present teachings.

FIG. 10 is a cross-sectional side profile view of an illustrative portable vacuum device in accordance with the present teachings.

FIG. 11a is across-sectional side profile view of an illustrative portable vacuum device in accordance with the present teachings.

FIG. 11b is a cross-sectional side profile view of the portable vacuum device of FIG. 11a shown connected to the insertion device of FIG. 1.

DETAILED DESCRIPTION

Figure 1:
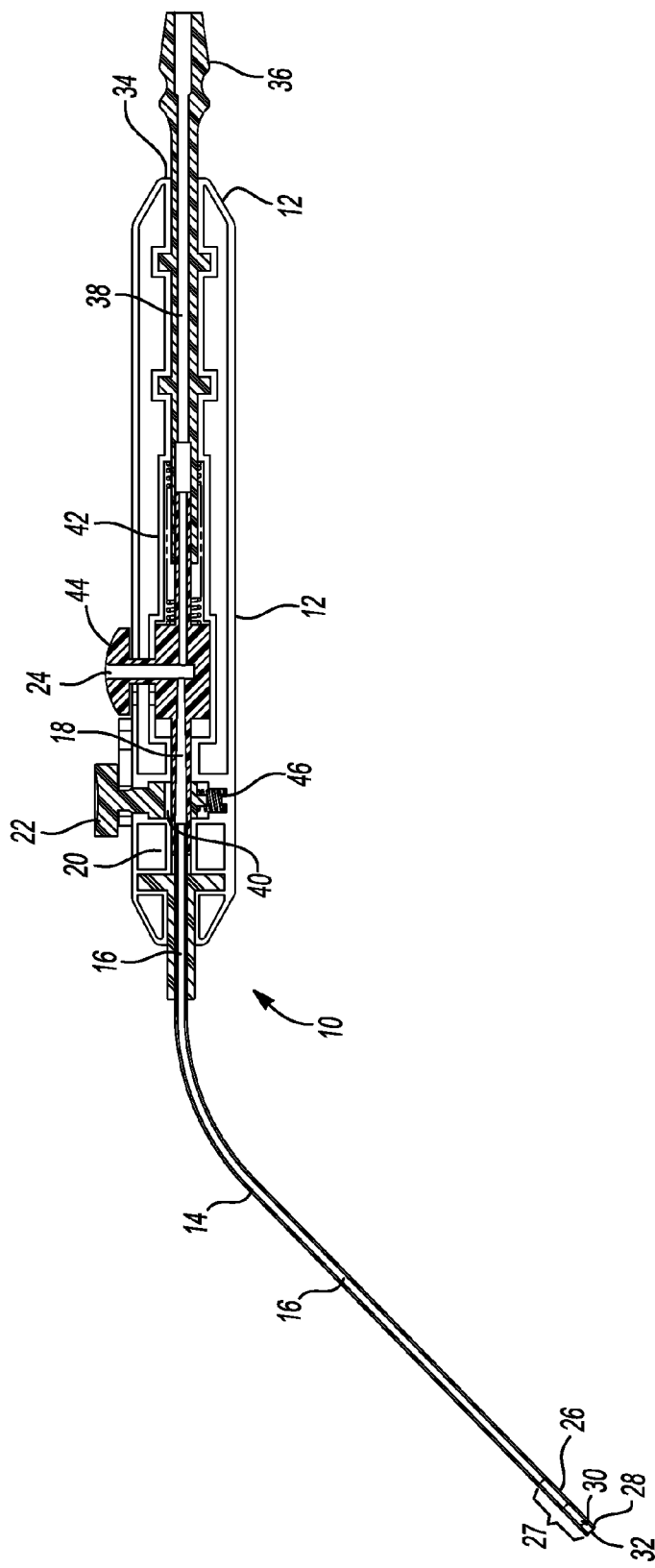
FIG. 1 is a cross-sectional profile view of an illustrative example of an insertion device in accordance with the present teachings.

The present teachings pertain generally to improved ear ventilation tube insertion device and associated ventilation tubes. The device facilitates nearly simultaneous tympanic membrane perforation, tube insertion, and aspiration. The speed with which the insertion an aspiration process takes place allows for minimized patient discomfort.

Accordingly, in one aspect of the teachings there is contemplated an insertion device. The insertion device may include a rigid shaft having a first terminal end and a second terminal end. The rigid shaft contains a tube located therein (the rigid shaft preferably substantially enclosing the tub), which may be a flexible tube and connects a plunger assembly at one end of the device with a ventilation tube and blade assembly at an opposing end of the device. The first terminal end of the shaft may include a shaft tip (e.g., a shaft transparent tip or distal tip) which houses (or is adapted to house) a ventilation tube, a perforating blade, and at least a portion of a flexible tube. The shaft tip may be formed of a transparent material so that a user may view an insertion site during insertion of ventilation tubes into an ear canal. The second terminal end of the shaft may contain a plunger/tube joint where the tube located within the rigid shaft is connected to a plunger such at activation of the plunger will cause longitudinal movement of the tube.

The plunger assembly may include a spring loaded plunger which connects to the flexible tube at the plunger/tube joint. The plunger assembly may further include one or more buttons, openings, or similar activation mechanisms to cause one or more perforation, insertion, retraction and/or aspiration steps. The plunger assembly may include a plunger release mechanism which may be in the form of a button, switch, opening, or the like (e.g., a plunger release button or plunger activation button). The plunger release mechanism may include one or more components for causing movement (e.g., release) of the plunger. Such components may be interconnected with the plunger such that movement of the components causes release of the plunger. As an example, the plunger release mechanism may include one or more structures (e.g., flats, plunger flats, or a releasable latching mechanism) that are engaged with the plunger release mechanism and thereby assist in maintaining the plunger in a ready position, whereby movement of the structures facilitates a forward motion of the plunger. Activation of the plunger release mechanism (by depression or sliding of a button, flipping of a switch, covering/uncovering an opening or the like) may cause disengagement with the plunger flats and thus the release of the plunger. The plunger release mechanism may also include components that facilitate the return of the mechanism to a ready state. For example, the release mechanism may include a lever, spring, or the like.

The plunger assembly may also include a plunger retrieval mechanism which assists in returning the plunger to a ready state after activation of the plunger release mechanism. The retrieval mechanism may be similar to the release mechanism in that it may be a button, switch, opening, or the like. Alternately, the plunger retrieval mechanism may be connected as one unit with a suction tube such that release of the plunger may be accomplished by pulling in a rearward direction on the suction tube connector. The plunger retrieval mechanism (e.g., the plunger retrieval button) may be activated by depression or sliding of a button, flipping of a switch, covering/uncovering an opening, or the like. Such activation may engage the spring loaded plunger by pulling the plunger downward toward the bottom of the device. This downward motion may cause compression or loading of a plunger spring thereby preparing the plunger for a subsequent release. Depression, actuation, or movement of the plunger retrieval mechanism may re-engage the plunger flats to hold it in a ready position.

The plunger spring preferably contacts the plunger directly and may contact the plunger in one or more locations. The plunger spring may be arranged so that upon release of the plunger (via the plunger release mechanism discussed above), the plunger spring pushes the plunger in a forward direction so that any component in contact with the plunger (which may include the flexible tube) also moves in a forward direction. In one embodiment, the plunger may include one or more widened portions or ledges and the plunger spring may be located in contact with those widened portions.

Upon release of the plunger and forward movement of the flexible tube through the rigid shaft, one or more components within the transparent tip (e.g., those components in direct or indirect contact with the flexible tube) may also move forward. Thus, upon release of the plunger, the vent tube and any associated perforating blades may also be pushed in a forward direction. Preferably, the perforating blade is arranged so that it enters an ear canal prior to or substantially simultaneous with the ventilation tube. In other words, the perforating blade may enter first to contact the tympanic membrane prior to insertion of the ventilation tubes.

To achieve this, the ventilation tube may be fitted with a perforating blade, such that the perforating blade is located on a front end of the ventilation tube. Thus, upon insertion of the ventilation tube into an ear canal (by means of the plunger release mechanism), the perforating blade will enter first. As such, the perforating blade remains attached to the ventilation tube even after ventilation tube insertion. The perforating blade may be formed of a material so that it softens once the ventilation tube is inserted. The perforating blade, or portions of it, may be formed of a material that is bio-absorbable, such that it will disintegrate over time. As an alternative, the insertion device may include a perforating blade that perforates the tympanic membrane prior to ventilation tube insertion, but retracts during insertion. To allow for retraction, the ventilation tube may be formed with one or more slots along a side of the tube. The slots may be longitudinal slots and there may be one, two, three slots or more. The slots may be substantially parallel to one another. The slots may approach a very thin silt, in which the surface area of the two sides of the slit are substantially in contact, so as to discourage the growth of tissue or buildup of fluids there between. The distal ends of the vent tube slit may be flexible so as to allow for the passage of the perforating blade there between and a return to a closed or substantially dosed state wherein the surface area of the two sides of the slit are substantially in contact after perforation is complete.

As a result, the shaft transparent tip which receives the ventilation tubes may include slots as well, regardless of the type of ventilation tube utilized. For example, the ventilation tube with attached perforating blade may be arranged within the shaft transparent tip so that the blade is coplanar with the slots. The blades may thus be located adjacent to or within the openings formed by the slots. Alternatively, the slots may be aligned with and therefore substantially parallel to the slots associated with a ventilation tube that is formed to receive a retractable blade.

The shaft transparent tip or a portion thereof may be arranged at a skew angle in relation to the rigid shaft, such that the tip extends in a direction that is neither parallel nor perpendicular to the rigid shaft. The shaft transparent tip or a portion thereof may be adapted for rotation in an effort to facilitate more precise location of the ventilation tubes. A locking mechanism may also be included so that the rotation occurs only when intended so that the tip does not move during insertion of the ventilation tubes. Such modification to the shaft transparent tip may assist in customizing the insertion procedure depending on a patient's anatomy or depending on the preferences of the user.

The ventilation tube is preferably located in contact with the first terminal end of the rigid shaft. The perforating blade may be attached directly to the spring loaded plunger. The ventilation to may be located in contact with the first terminal end of the rigid shaft and the ventilation tube may include one more longitudinal slots through which the perforating blade extends during use of the device.

Upon insertion of the ventilation tube the device may be fitted with components to allow for immediate aspiration after the ventilation tube is inserted. A suction tube may be located within the device and may be specifically located within the handle portion of the device. A suction control mechanism may also be located within the device, such that the suction control mechanism is in communication with the suction tube. The suction control mechanism may include an opening, a button, a switch, or the like. The suction control mechanism may include an opening located on, within, or adjacent to one or more of the plunger release mechanism plunger retrieval mechanism. Preferably, the suction control mechanism is an opening formed on the plunger retrieval mechanism. During aspiration, a user may control the suction by covering/uncovering the opening as necessary. The components for aspiration may be in communication with a suction device that is located external the insertion device, such as an in-line vacuum source at a clinic/hospital. A suction tube connector may be included within the insertion device for connecting the suction device to the insertion device.

Alternatively, in the event that such a vacuum source is not available, a portable source for providing the necessary suction force during aspiration may be provided. However, the connection of such portable devices to the insertion device may be formed to avoid unwanted movement of the insertion device or the application of undesired positive pressure to the insertion device. One such portable device may include a squeeze bulb for connecting to the insertion device via a length of tubing. The tubing may be such that it is long enough that the length would provide isolation of the insertion device from any squeezing/pumping activity. One-way pneumatic rents may be located adjacent the squeeze bulb, installed so that squeezing the bulb would evacuate air out of the bulb to the atmosphere at a first proximal end and releasing the bulb would impart a vacuum to a second distal end where the tubing is connected. An in-line collection filter may be located within the tubing, the in-line filter having one or more one-way valves to prevent the application of positive pressure to the insertion device. The collection filter may be used to collect and contain aspirated biological media and prevent the aspirate from passing on to suction devices such that the suction devices can be reused and such that air flow is not prevented following filtration. The use of such a device provides the necessary suction upon release of the bulb as opposed to the squeezing of the bulb. As such, it may be desirable to fit the portable vacuum device with an in-line, normally closed push-button valve which would maintain the vacuum within the bulb and only apply the vacuum when required (by pressing the in-line valve button), thus applying the vacuum in an active pressing step as opposed to a release step.

Another possible portable vacuum device may include use of a bellows and hand grip configuration where squeezing the hand grip expands the bellows, providing vacuum as a direct response to the squeezing action. The bellows may be deflated either by a spring configured with the handgrip, or a self-deflating bellows that would return the handgrip and bellows to a deflated and ready-to-squeeze condition. Alternatively, a bellows with an associated expanding spring having a normally closed push button valve as described with reference to the squeeze bulb device could be compressed and then available to provide vacuum force by pressing the valve button. The bellows configurations may be integrated with the insertion device and configured to provide a vacuum force from the squeeze of a trigger or button. Alternatively the bellows device may be configured to provide a vacuum upon release of a trigger or button. A push button valve may be included as necessary.

The portable vacuum device may include a syringe, such that the syringe may provide a vacuum when assembled with a handgrip designed to withdraw the syringe plunger when squeezed. The handgrip may also include a spring that would be designed to re-expand the handgrip while pushing the syringe plunger back inward. One possible design the handgrip would allow for the mounting and dismounting of a standard syringe. It may also be necessary to have a one-way valved adaptor at the output of the syringe that would vent positive pressure from the syringe to the atmosphere. It may also be necessary to have an in-line one-way valve which would prevent the application of unwanted positive pressure to the insertion device. An in-line collection filter in the tubing is desirable, the in-line filter having one or more one-way valves to prevent the application of positive pressure to the insertion device. Alternatively, a syringe could be loaded into a device with a spring-loaded plunger retraction feature. This feature could be pre-set and released to apply vacuum pressure when desired. Alternatively, an in-line normally closed pushbutton valve may be utilized which would maintain a vacuum in the syringe until the pushbutton valve was opened and applied to the insertion device via the filter and tubing.

An automated method of providing a portable vacuum source may be included. Such a device may be a small, self-contained vacuum pump with a powered drive mechanism, such as a motor or oscillating solenoid. The portable automated device may be battery powered and may be turned on for the duration of the procedure, or only when needed. The vacuum pump may be separated and vibrationally isolated from the insertion device via a tube of sufficient length. Thus, the size of the vacuum pump may not be limited, as it may be in handheld configurations. Yet another option for the use of a powered vacuum pump is to integrate a small, battery or otherwise powered pump into the handle of the insertion device or configure a pump that may be attached to the insertion device handle. Such a configuration may be easily held, light, compact and very low in vibration and noise. An attachable pump could be reusable.

Upon insertion of a first ventilation tube, the insertion device may be adapted to receive a second ventilation tube and to insert a second ventilation tube. More specifically, the shaft transparent tip may be adapted to receive a second ventilation tube after a first ventilation tube has been expelled from within the shaft transparent tip. The first ventilation tube may be expelled from the shaft transparent tip upon depression of the plunger release button and the shaft transparent tip may receive the second ventilation tube after depression, actuation, or movement of the plunger retrieval button. The shaft transparent tip may then be aligned with a second ventilation tube such that the blade runs parallel to the slots of the shaft transparent tip. Pressure may then be applied until the second ventilation tube snaps into place in a groove within the shaft transparent tip. A kit including a pair of ventilation tubes is thus envisioned. The kit may include a first and second ventilation tube located therein. In one embodiment, the tubes may be packaged in a capsule, the capsule having a first end for holding the first ventilation tube and a second opposing end for holding the second ventilation tube, each end including a removable cap for accessing the first and second ventilation tubes.

The teachings herein also contemplate methods for use of the insertion device. Such methods may include providing a device in a ready position and locating a ventilation tube within the transparent shaft tip of the device. The transparent shaft tip being preferably attached to the first terminal end of the rigid shaft and the rigid shaft may contain at least a portion of a plunger assembly. The plunger, in a ready position, may compress or slightly compress a plunger spring. A portion of the ventilation tube may then be located proximate an ear canal. The plunger release button is depressed, whereby the movement of the plunger release button causes a release of one or more plunger flats, and the release of the plunger flats allows a compressed plunger spring to push the plunger assembly forward so that the ventilation tube enters into the ear canal. The plunger retrieval button is slid toward the proximal end of the device to return the device to the ready position. Once in the ready position, the shaft transparent tip may receive a second ventilation tube for insertion into a second ear canal.

The insertion device may be provided as a sterilized disposable piece in a packaging intended for opening by an end user in a doctor's office or in an operating room. The handle may be made up of two separate halves connected with mating features that secure the housing together. The handle may have a left handle half and a right handle half. Once the two handle halves are connected together and the mating features have snapped, clicked, or otherwise joined together, the two handle halves of the insertion device may not be separated from each other without breaking some of the mating features or some of the components of the insertion device. The insertion device may be provided with one ventilation tube loaded into the tip. Two additional ventilation tubes may be provided within a ventilation tube housing, which may be a capsule or other containment device, which may be provided together in a packaging with the insertion device or in a separate sterile packaging to the end user.

Turning now to the drawings to illustrate examples of embodiments of the present teachings, as shown for example in FIG. 1, the insertion device 10 includes a handle portion 12 and rigid shaft 14. A flexible tube 16 is located within the rigid shaft, the flexible tube joined with at least a portion of a spring loaded plunger 18 at a tube/plunger joint 20. The spring loaded plunger 18 is in direct communication with a plunger release button 22 and a plunger retrieval button 44. A first terminal end 26 of the insertion device includes a distal tip 27 including a shaft transparent tip 28. The shaft transparent tip includes a ventilation tube 30 located therein and a perforating blade 32 associated with the ventilation tube 30.

At the second terminal end 34 of the insertion device, a suction tube connector 36 extends from the device and is connected to a suction tube 38 which is at least partially enclosed within the handle portion 12. Suction tube 38 is located inside the device handle proximal end and a proximal end of the plunger may slide inside the suction tube distal hole. Suction tube 38 may be cylindrical, rectangular, or any other shape that reasonably allows for aspiration via suction connector 36. A suction tube seal is provided between plunger retrieval button 44 and suction tube 38 to ensure that the slidable engagement is properly sealed. The suction tube seal may be in the form of an o-ring, encompassing flexible membrane, grease, or other lubricant, and provides air sealing to allow for effective suctioning at the distal end of the insertion device.

Depression of the plunger release button 22 causes engagement of one or more plunger flats 40 such that the movement of the plunger flats initiates release of a plunger spring 42. Plunger flats 40 align with flats within plunger release button 22 (not shown) and act as a guide for the plunger release button 22 such that the button cannot be rotated. The engaged plunger spring exerts a force on the spring loaded plunger 18. The force causes the spring loaded plunger to push the ventilation tube 30 outward from the shaft transparent tip 28. The ventilation tube 30 may be located in an ear canal upon depression of the plunger release button. Simultaneous to depression of the plunger release button 22, the plunger retrieval button 44 may slide forward. Upon insertion of ventilation tube 30, the plunger retrieval button 44 may be slid toward the proximal end of the device, causing the plunger spring 42 and spring loaded plunger 18 to retract and return to an original start position (e.g., the position prior to depression of the plunger release button 22). on realignment of the plunger flats with the plunger release button, the plunger release button may then return to an original start position and engage the flats of the plunger, thus holding the plunger in an original start position. A suction control opening 24 located on the plunger retrieval button 44 can be covered and/or uncovered by a user to control aspiration of the ear canal. When a user's finger is placed over plunger retrieval button 44, suction control opening 24 is typically covered and suction becomes possible. When suction control opening 24 is uncovered, suction capability at the distal tip is severely reduced, depending on the size of the suction control opening. The plunger retrieval button 44 may be actuated by different means, including a pull handle, a knob, a press button which internally slides the release mechanism back to a ready position, or other feature located near the proximal end of the device to return the release mechanism to a ready position. When the plunger retrieval button 44 is moved backward in a sliding motion to an original start position and held in place by the plunger release button 22 which has returned to its original start position, a second ventilation tube may then be located within the shaft transparent tip 28 for insertion into a second ear canal.

Figure 2:
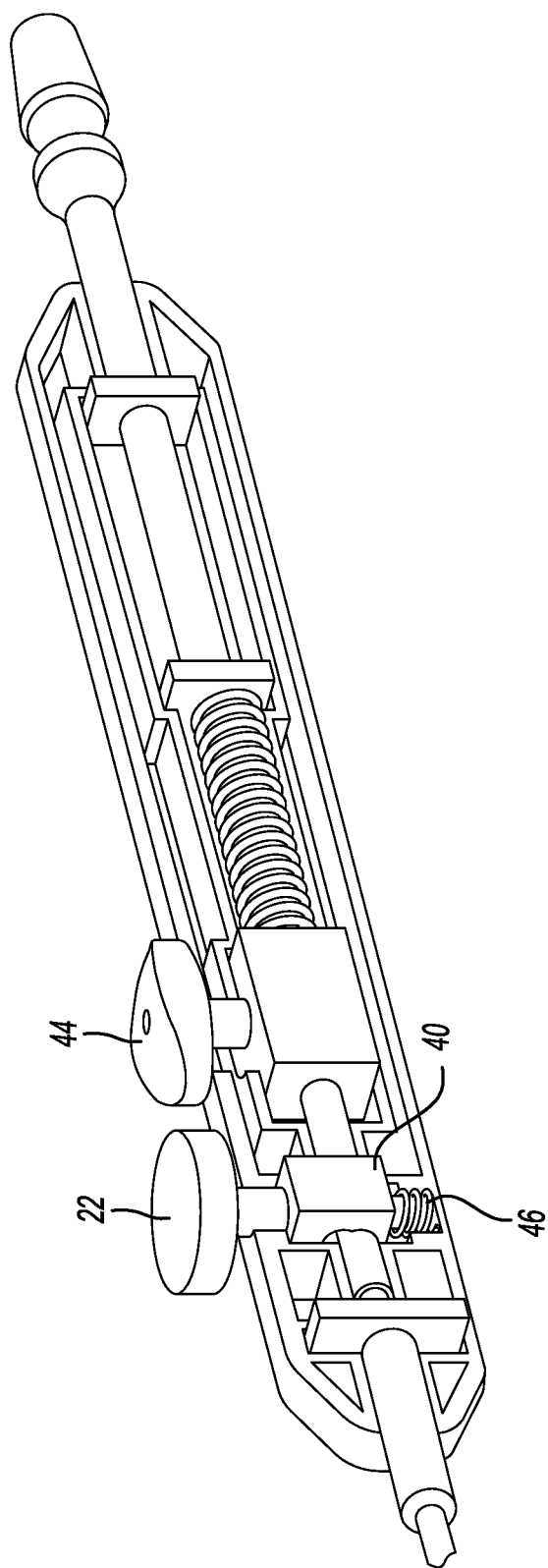
FIG. 2 is a cross-sectional profile view of illustrative examples of a plunger release button and a plunger retrieval button.

With reference to FIG. 2, the locations of the plunger release button 22 and plunger retrieval button 44 may be such that the plunger retrieval button is located just below the plunger release button. The plunger release button may be in communication with a rebase button spring 46 and one or more plunger flats 40.

Figure 3:
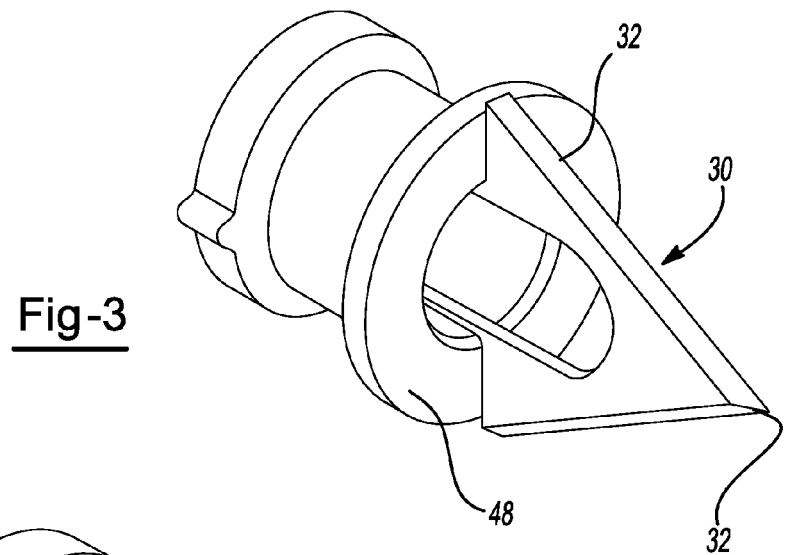
FIG. 3 is a perspective view of an illustrative example of a ventilation tube and perforating blade in accordance with the present teachings.
Figure 4:
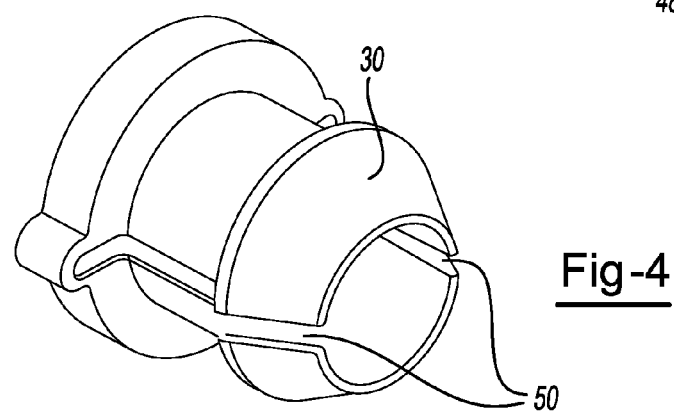
FIG. 4 is a perspective view of an illustrative example of a ventilation tube including longitudinal slots.

FIGS. 3 and 4 depict illustrative examples of ventilation tubes in accordance with the present teachings. As shown for example at FIG. 3, the ventilation tube 30 includes a perforating blade 32 connected to a first end 48 of the ventilation tube, so that the perforating blade enters an ear canal and remains connected to the ventilation tube after insertion of the ventilation tube. As an alternative embodiment, FIG. 4 shows a ventilation tube including one or more longitudinal slots 50. The longitudinal slots are adapted for receiving a perforating blade (not shown) during insertion of the ventilation tube into an ear canal. During insertion, activation of the spring loaded plunger (not shown) causes a perforating blade to extend into and through the longitudinal slots 50 so that the perforating blade pierces the tympanic membrane and then retreats back through the longitudinal slots.

Figure 5:
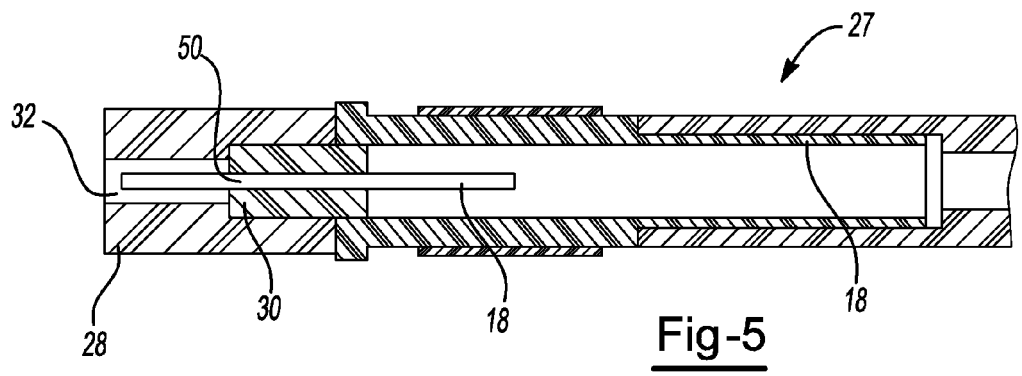
FIG. 5 is a cross-sectional profile view of an illustrative distal tip assembly in accordance with the present teachings.

FIG. 5 shows an illustrative example of the distal tip 27 of an insertion device for utilizing the ventilation tube of FIG. 4. The ventilation tube 30 is shown within the shaft transparent tip 28. The perforating blade 32 extends through a longitudinal slot 50 and contacts the spring loaded plunger 18.

Figure 6:
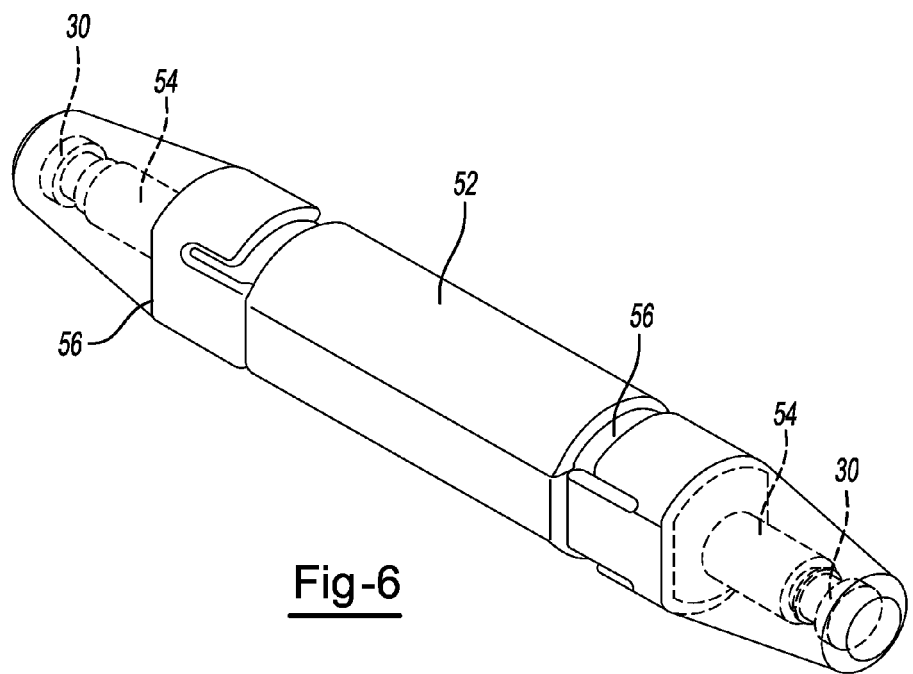
FIG. 6 is a perspective view of an illustrative packaging containing ventilation tubes at either end for reloading the insertion device of FIG. 1.

As shown at FIG. 6, a pair of ventilation tubes 30 may be located into a ventilation tube housing 52. The ventilation tube housing 52 may be provided in a capsule form as shown, whereby each end 54 of the capsule contains one ventilation tube 30 covered by a cap portion 56.

FIGS. 7-11 depict various exemplary portable vacuum device that may be used with the insertion device to provide tape necessary vacuum pressure for aspiration during use of the insertion device. As shown for example at FIG. 7, the portable vacuum device 58 includes a squeeze bulb 60, an outflow valve 62, and an inflow valve 64. A tubing 66 may be included for connecting the vacuum device to the insertion device (not shown). A push-button activated valve 68 may be located adjacent the inflow valve. A collection filter 70 may also be included, the collection filter being located adjacent one or more one-way valves 72 to prevent the application if unwanted positive pressure to the insertion device.

Figure 7:
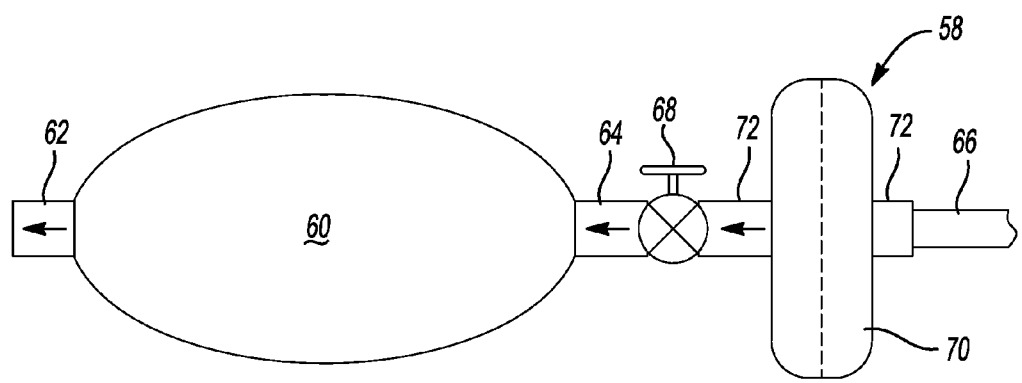
FIG. 7 is a perspective view of an illustrative portable vacuum device in accordance with the present teachings.
Figure 8A:
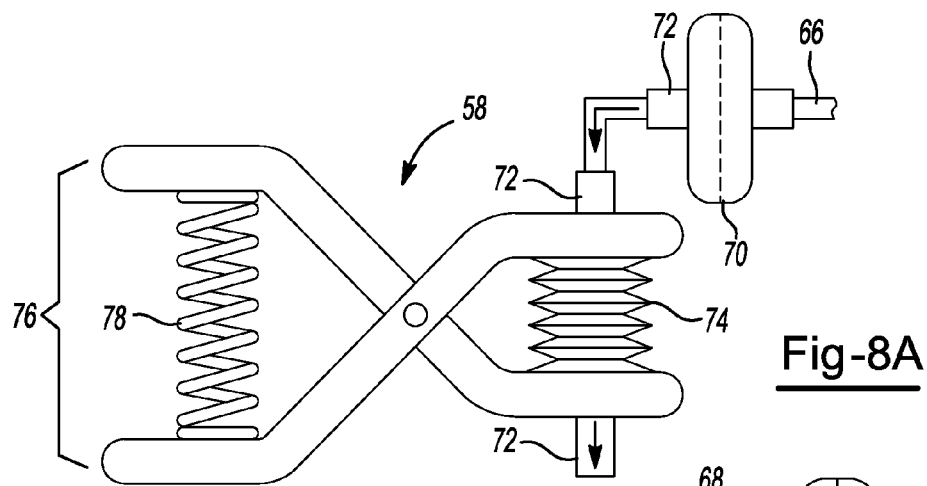
FIG. 8a is a perspective view of an illustrative portable vacuum device in accordance with the present teachings.
Figure 8B:
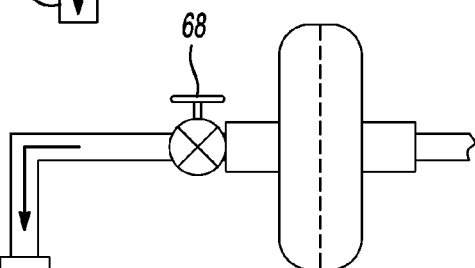
Figure 8B:
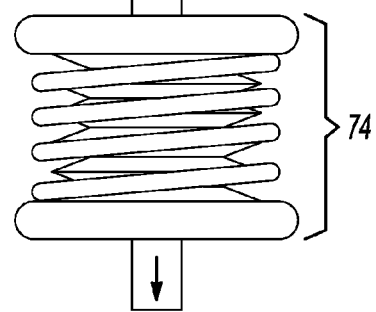
Figure 8C:
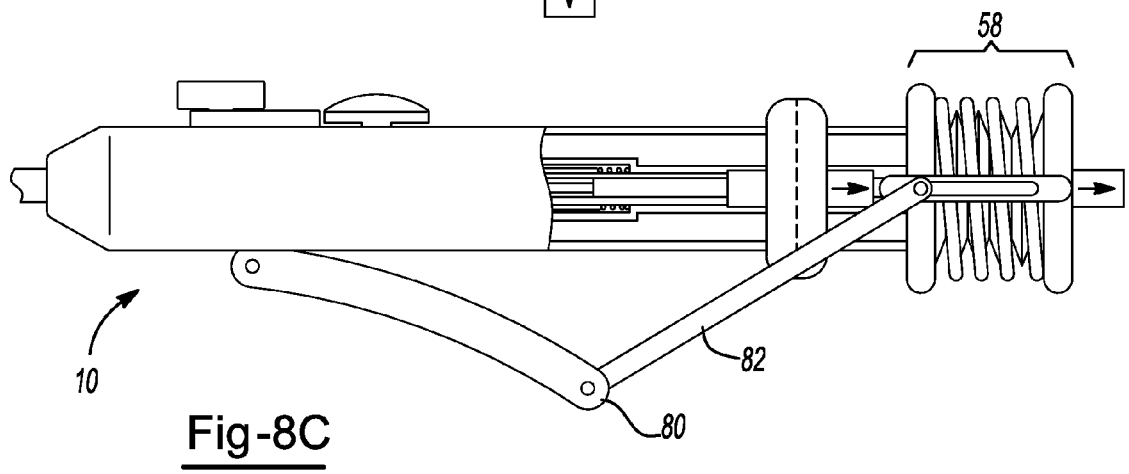
FIG. 8c is a cross-sectional side profile view of the portable vacuum device of FIG. 8b shown connected to the insertion device of FIG. 1.

The device of FIG. 7 may be modified to form the devices shown at FIG. 8a-8c. As shown in FIG. 8a, the squeeze bulb of the portable vacuum device 58 may be replaced by a bellows 74 and hand grip 76. The hand grip may include a spring configuration 78 and the bellows may be located adjacent one or more one-way valves 72 and a collection filter 70 also located adjacent one or more one-way valves 72. A tubing 66 may also be included for connecting the portable vacuum device to the insertion device (not shown). FIG. 8b shows a modified bellows device without a hand grip. The bellows 74 may instead be controlled by a push-button activated valve 68. FIG. 8c shows the device of FIG. 8b connected the insertion device 10. A trigger 80 may be connected to the portable vacuum device 58 via an arm portion 82, thereby activating the vacuum force.

FIG. 9 depicts a syringe configuration for the portable vacuum device 58, whereby a syringe 84 is utilized to provide the requisite vacuum force via a hand grip 88. The hand grip may include a spring 88 for returning the hand grip to its original position after compression of the hand grip. A valved adaptor 90 may be adjacent a terminating end 92 of the syringe for preventing the application of positive pressure to the insertion device (not shown). As with previous embodiments of the portable vacuum device, a collection filter 70 and one or more on-way valves 72 may also be included.

FIG. 10 shows an alternative syringe vacuum design whereby the portable vacuum device 58 is loaded into a secondary platform 94 (e.g., a pre-load base) for receiving the syringe 84. The syringe may be located within the platform by contacting one or more grip or snap arms 97 that extend upward from the secondary platform. Grip or snap arms may provide a snap-in or alternate locking mechanism to hold syringe 84 in place on platform 94. The secondary platform may include a spring loaded plunger retraction feature including a spring 96, slider release mechanism 98 (for maintaining the location of the syringe plunger 95 until release), and plunger retraction slider 99. The syringe plunger contacts plunger retraction slider 99 for preventing and or facilitating movement of the syringe plunger as needed. Plunger retraction slider 99 may hold plunger in place prior to downward pressure being applied to slider release mechanism 98, causing spring 96 to release and plunger to extend from syringe 84, creating a suction felt at the distal tip of the insertion device. A push-button activated valve 88 may be included and located adjacent one or more one-way valves 72.

FIGS. 11a and 11b depict a portable vacuum device 58 having a motorized port pie vacuum pump 100. The vacuum pump may include an activation button 102 and one or more one-way valves 72 as shown at FIG. 11a. FIG. 11b shows the motorized portable vacuum pump attached to the insertion device 10 via a tubing 66 and in contact with the handle portion 12 of the insertion device.

As to all of the foregoing general teachings, as used herein, unless otherwise stated, the teachings envision that any member of a genus (list) may be excluded from the genus; and/or any member of a Markush grouping may be excluded from the grouping.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

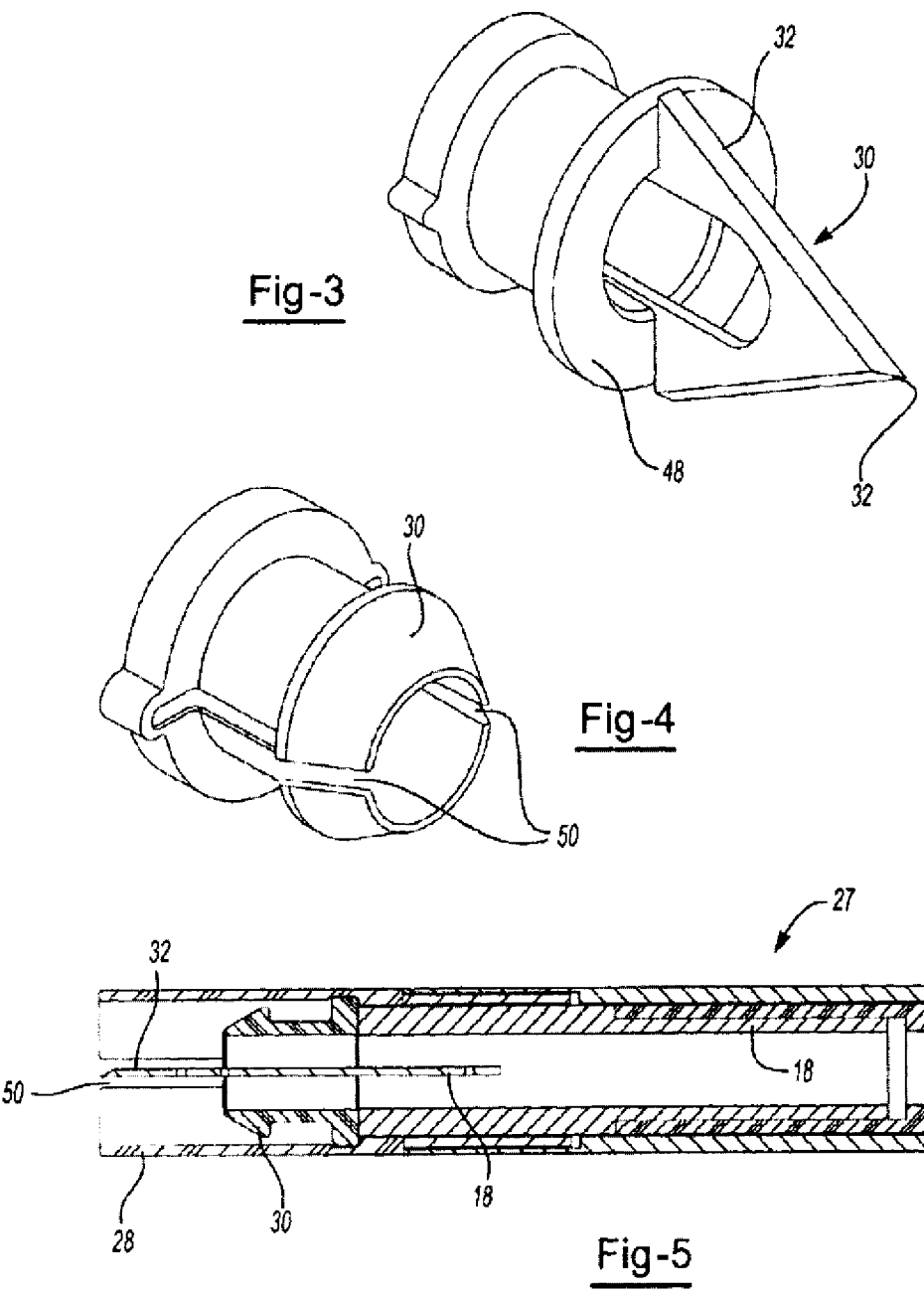

What is claimed is:
1. A device comprising:
 a. a rigid shaft having a first terminal end and a second terminal end;
 b. a flexible tube substantially enclosed within the rigid shaft;
 c. a spring-loaded plunger, at least a portion of which is joined with the flexible tube;

d. a plunger release button adapted for engaging the plunger and releasing the plunger so that upon depression of the release button, the plunger extends toward the first terminal end of the rigid shaft;

e. a plunger retrieval button for returning the device to a ready position;

f. a suction tube located inside a device handle proximal end;

g. a plunger retrieval button suction hole located on a top portion of the plunger retrieval button and protruding down to meet with the suction tube; and h. a suction connector located adjacent the second terminal end of the rigid shaft and adapted for receiving a tubing for connecting a vacuum device.

2. The device of claim 1, wherein a first ventilation tube is located in contact with the first terminal end of the rigid shaft.

3. The device of claim 2, wherein the ventilation tube is formed to include a perforating blade for tympanic membrane perforation.

4. The device of claim 3, wherein the perforating blade or portions of it comprise a bio-absorbable material so that the perforating blade or portions of it disintegrate or soften over time.

5. The device of claim 1, wherein a perforating blade is attached directly to the spring loaded plunger.

6. The device of claim 5, wherein a ventilation tube is located in contact with the first terminal end of the rigid shaft and the ventilation tube includes one or more longitudinal slots through which the perforating blade extends during use of the device.

7. The device of claim 1, wherein the plunger release button is located adjacent to the plunger retrieval button.

8. The device of claim 1, wherein the plunger release button includes components located on opposing sides of a bottom portion of the plunger release button for causing movement of the plunger.

9. The device of claim 8, wherein the spring loaded plunger and the plunger release button engage one or more plunger internal flats and upon depression of the plunger release button the one or more plunger internal flats are released which allows the spring loaded plunger to move in response to a force applied thereto.

10. The device of claim 1, wherein the retrieval button is spring loaded.

11. The device of claim 1, including a handle having a left handle half and a right handle half.

12. The device of claim 1, wherein the first terminal end of the rigid shaft includes a shaft tip that receives a ventilation tube.

13. The device of claim 1, wherein a shaft tip is adapted to receive a second ventilation tube after a first ventilation tube has been expelled from within the shaft tip.

14. The device of claim 2, wherein the first ventilation tube is expelled from a shaft tip upon depression of the plunger release button and the shaft tip receives a second ventilation tube after sliding or actuation by other means of the retrieval button toward the proximal end of the device.

15. The device of claim 13, wherein the shaft tip is transparent.

16. The device of claim 1, wherein the suction tube is connected to either a permanent vacuum device or a portable vacuum device.

17. A kit comprising the device of claim 1, wherein the kit includes a first and second ventilation tube located within a capsule, the capsule having a first end for holding the first ventilation tube and a second opposing end for holding the second ventilation tube, each end including a removable cap for accessing the first and second ventilation tubes.

18. A device comprising:

a. a rigid shaft having a first terminal end and a second terminal end;

b. a flexible tube substantially enclosed within the rigid shaft;

c. a spring-loaded plunger, at least a portion of which is joined with the flexible tube;

d. a plunger release button adapted for engaging the plunger and releasing the plunger so that upon depression of the release button, the plunger extends toward the first terminal end of the rigid shaft:

e. a plunger retrieval button for returning the device to a ready position;

f. a suction tube located inside a device handle proximal end;

g. a plunger retrieval button suction hole located on a top portion of the plunger retrieval button and protruding down to meet with the suction tube; and h. a suction connector located adjacent the second terminal end of the rigid shaft and adapted for receiving a tubing; and i. a portable vacuum device in communication with the suction connector via the tubing, the portable vacuum device including one or more valves for controlling the application of vacuum force to the device.

* * * * *

UNITED STATES PATENT AND TRADEMARK OFFICE
CERTIFICATE OF CORRECTION

PATENT NO.        : 8,795,290 B2
APPLICATION NO.   : 13/773778
DATED             : August 5, 2014
INVENTOR(S)       : Gregory S. Konstorum et al.

It is certified that error appears in the above-identified patent and that said Letters Patent is hereby corrected as shown below:

In the Drawings

Delete Drawing Sheet 3 of 7 and substitute therefore with the attached Drawing Sheet 3 of 7.

Signed and Sealed this
Twenty-seventh Day of January, 2015

Michelle K. Lee
*Deputy Director of the United States Patent and Trademark Office*